United States Patent
Meah

(10) Patent No.: US 6,432,040 B1
(45) Date of Patent: Aug. 13, 2002

(54) IMPLANTABLE ESOPHAGEAL SPHINCTER APPARATUS FOR GASTROESOPHAGEAL REFLUX DISEASE AND METHOD

(76) Inventor: Nizam N. Meah, 236 Plum Cir., Lake Jackson, TX (US) 77566

( * ) Notice: Subject to any disclaimer, the term of this patent is extended or adjusted under 35 U.S.C. 154(b) by 4 days.

(21) Appl. No.: 09/661,978

(22) Filed: Sep. 14, 2000

(51) Int. Cl.7 ............................................. A61F 2/04
(52) U.S. Cl. ................... 600/37; 623/23.65; 623/23.67
(58) Field of Search ............................... 600/29–32, 37; 128/897, 898, DIG. 25; 623/23.65, 23.67

(56) References Cited

U.S. PATENT DOCUMENTS

| | | | | |
|---|---|---|---|---|
| 3,863,622 A | * | 2/1975 | Buuck ........................... | 600/31 |
| 4,222,377 A | * | 9/1980 | Burton .......................... | 600/31 |
| 4,408,597 A | * | 10/1983 | Tenney, Jr. .................... | 600/31 |
| 4,412,530 A | * | 11/1983 | Burton .......................... | 600/31 |
| 4,419,985 A | * | 12/1983 | Trick ............................ | 600/31 |
| 4,437,457 A | * | 3/1984 | Trick et al. ................... | 600/31 |
| 4,784,660 A | * | 11/1988 | Fischell .................. | 600/31 X |
| 4,878,889 A | * | 11/1989 | Polyak .......................... | 600/31 |
| 4,881,939 A | * | 11/1989 | Newman ....................... | 600/31 |
| 4,994,020 A | * | 2/1991 | Polyak .......................... | 600/31 |
| 5,006,106 A | * | 4/1991 | Angelchik .................... | 600/37 |
| 5,316,543 A | * | 5/1994 | Eberbach ...................... | 600/37 |
| 5,403,326 A | * | 4/1995 | Harrison et al. ......... | 128/898 X |
| 5,478,305 A | * | 12/1995 | Craggs ......................... | 600/31 |
| 5,509,888 A | * | 4/1996 | Miller .......................... | 600/29 |
| 5,562,598 A | * | 10/1996 | Whalen et al. ................ | 600/29 |
| 5,893,826 A | * | 4/1999 | Salama ......................... | 600/31 |
| 6,067,990 A | * | 5/2000 | Kieturakis ................... | 128/898 |
| 6,095,969 A | * | 8/2000 | Karram et al. ................ | 600/31 |
| 6,238,335 B1 | * | 5/2001 | Silverman et al. ............ | 600/29 |

* cited by examiner

*Primary Examiner*—John P. Lacyk
*Assistant Examiner*—Joseph A. Cadugan
(74) *Attorney, Agent, or Firm*—John R Merkling

(57) ABSTRACT

An implantable esophageal sphincter apparatus with an adjustable band to be placed at the lower part of the esophagus. The inflation of the band, or sphincter body, can be increased or decreased to adjust the tightness of the device. The inflatable sphincter body may be wrapped around the esophagus and may be connected to an inflation device with a fluid reservoir. The inflation device may have a pump mechanism that will respond to external control to increase or decrease the inflation of the sphincter body. The sphincter apparatus will be held in place at the area of implantation by sutures and by fenestration mechanisms, which will allow ingrowths of tissue or fibrous elements of the body around the sphincter apparatus or into porous materials on the sphincter apparatus. The apparatus may also include a circumferential shield on a distal side of the sphincter apparatus. The shield is adapted to fit against the distal or lower side of the patient's diaphragm and inhibits the development of a hiatus hernia, that is, a protrusion of the stomach past the diaphragm through the passage for the esophagus.

35 Claims, 3 Drawing Sheets

IMPLANTABLE ESOPHAGEAL SPHINCTER APPARATUS FOR GASTROESOPHAGEAL REFLUX DISEASE AND METHOD

FIELD OF THE INVENTION

The present invention relates to an implantable apparatus for use treating gastroesophageal acid reflux and particularly to an artificial sphincter for the lower esophageal sphincter.

BACKGROUND OF THE INVENTION

Gastroesophageal reflux disease (GERD) is one of the most common medical illnesses in today's western society. Gastroesophageal reflux occurs when the contents of the stomach, including acids and digestive fluids, leak back past the lower esophageal sphincter into the esophagus. This produces the sensation commonly referred to as "heartburn". Over prolonged periods, this condition can seriously compromise a person's health. Studies indicate that the incidence of gastroesophageal reflux is on the rise. For example, health care providers use Common Procedural Terminology ("CPT") codes to report treatment of certain conditions. In 1999, the CPT code for GERD was the most commonly used code from gastroenterologists' offices in the United States, indicating the prevalence of the condition. Incidence of this disease is similarly common in all parts of Europe and probably in any affluent society.

Currently, there are four options available for treatment of gastroesophageal reflux disease. These options are life-style modification, medication, surgery, and endoscopic fundoplication. Life-style modification comprises dietary changes and positioning of body so that, with the help of gravity, upward reflux of food and acid from the stomach is prevented. This treatment is seldom effective alone.

Medication is the most common treatment. Depending upon the degree of severity, a physician may prescribe medications ranging from less potent acid-blockers like Ranitidine (the so-called "Histamine 2 receptor blocker") to strong acid-production blockers like Prilosec (the Proton pump inhibitors—PPI). The results from treatment by medication are quite satisfactory in the majority of the cases. The problems are the need to take medication for the remainder of the patient's life with its enormous cost, the inconvenience of constantly keeping medicine with the patient, and the long-term concern about strong acid inhibition as a side effect of the medication. There is some data suggesting that atrophic gastritis may develop in some patients as a result of longterm therapy by medication. There is also a phenomenon called acid-rebound after discontinuation of medication. Finally, although medical therapy is effective against acid reflux conditions, it is not effective in controlling so-called "alkaline" or "bile" reflux.

Surgical therapy is currently recommended for the patients whose symptoms are not controlled by medication or for the patients who do not want to take long-term medication. Both traditional surgical procedures and laparoscopic approaches have been tried. Recent literature suggests that there may be significant long-term concerns with regard to the laparoscopic approach. Of course, the patient has to be physically fit to undergo such a procedure. In spite of cost, the difficulty of patient selection and the invasiveness involved, approximately 80,000 of these procedures were performed in the United States in 1999.

Endoscopic fundoplication is a very recent procedure done by the gastroenterologists. It consists of securing a suture in a purse-string-like configuration to the part lower part of the esophagus or upper part of the stomach, which basically creates an additional mechanical barrier to the contents of reflux from the stomach to esophagus. The data is very preliminary on this procedure and very few gastroenterologists are trained to perform it. Even in the best case, there are significant limitations to the procedure and some patients with large hiatus hernia will not qualify for this.

SUMMARY OF THE INVENTION

Despite multiple treatment options, treatment of GERD still needs improvement in long-term, low-cost treatment. Therefore, there is room for improvement in this area. I plan to accomplish this by an implantable esophageal sphincter apparatus, described below.

The apparatus comprises an adjustable band or sphincter body to be placed at the lower part of esophagus, most of the time over or around the Lower Esophageal Sphincter (LES) or around the very first part of stomach adjoining the esophagus. The internal inflation of the band can be increased or decreased to some extent, which in turn will adjust the tightness of the device. This will meet the need for some patients who might find it easier to swallow with a loose band and subsequently make it tighter to prevent reflux. The device will be of human-grade implantable material. The device will enhance the normal tone or pressure of the LES that naturally exists in the competent LES. In many cases, this natural tone is lost or these patients have more frequent LES relaxation than normal. This leads to chronic GERD. Placement of the esophageal band will prevent these phenomena from occurring and thereby prevent GERD. In short, this will mimic the normal human physiology by a mechanical means. This will promote the natural pressure barrier between the esophagus and stomach that naturally exists in normal physiologic state. The end result will be prevention of reflux and thereby GERD.

The apparatus will be implanted in a single surgical procedure. Most of the time, it could be placed by laparoscopic methods, which will minimize the invasiveness of the surgery and will lessen the duration of hospitalization. In some situations, a traditional open surgical method may be required. After gaining access in the abdominal or thoracic cavity either by laparoscopic or open surgical technique, the surgeon will isolate the area of the lower esophageal sphincter and the esophago-gastric junction (EGJ). During this procedure, an endoscope or a bougie of a satisfactory diameter placed per orally will give both guidance to the degree of tightness and protection to the esophagus. An inflatable sphincter body may be wrapped around the esophagus and may be connected to an inflation device with a fluid reservoir. The inflation device and reservoir may be implanted underneath the skin of the anterior chest wall or of the abdominal wall during the same surgical procedure with the sphincter body. The inflation device may have a pump mechanism that will respond to external control to increase or decrease the inflation of the sphincter body that, in turn, will either increase or decrease the tightness of the area upon which the sphincter body is placed (usually at the lower esophageal sphincter). The sphincter body may be held in place at the area of implantation by sutures and by fenestration mechanisms, which will allow ingrowths of tissue or fibrous elements of the body around the sphincter body or into porous materials on the sphincter body. After placement of the full device, the physician or surgeon will activate the pump mechanism and test the response of the mechanism before final closure.

The apparatus may also include a circumferential shield on a distal side of the sphincter body. The shield is adapted to fit against the distal or lower side of the patient's diaphragm and inhibits the development or re-occurrence of a hiatus hernia, that is, a protrusion of the stomach past the diaphragm through the passage for the esophagus. The apparatus, therefore, also provides a treatment for hiatus hernias.

A patient would undergo normal pre-surgical evaluation to determine suitability as a surgical candidate. Both gastroenterologists and surgeons with appropriate interests and competency in reflux treatment procedures should usually be consulted. Tests may include upper gastrointestinal endoscopy, and 24-hour pH and motility testing. These tests would provide objective evidence of GERD in the patient involved, including evidence of severity of damage, anatomic integrity of the organs involved, associated co-existing diseases that can effect patient's outcome and the extent and severity of reflux itself. In addition, certain radiological testing to image the upper gastrointestinal organs may also be an integral part of this evaluation.

After implantation of the apparatus, a physical examination of the patient may be conducted to reevaluate signs and symptoms as they pertain to the patient's pre-surgical and post-surgical outcome. If appropriate, endoscopy, 24-hour pH and motility studies may also be included in the post-surgical testing. Certain radiological testing, such as a CT scan, or upper gastrointestinal radiology, may be included.

It is an object of my invention, therefore, to provide an apparatus for the treatment of gastroesophageal reflux disease. Another object of my invention is to provide an apparatus having a prosthetic sphincter body for placement at or near the lower esophageal sphincter.

Yet another object of my invention is to provide a sphincter body that is inflatable to predetermined size.

Another object of my invention is to provide an artificial sphincter body that cannot be closed beyond a predetermined minimum orifice size. A further object of my invention is to provide control mechanisms for controlling the size of the sphincter body.

Another object of my invention is to provide an artificial sphincter body for the esophagus with a gap or opening to allow the sphincter body to be placed around the esophagus.

It is also an object of my invention to provide an implantable prosthetic sphincter having a shield to prevent development or re-occurrence of hiatus hernias of the stomach through the diaphragm.

These and other features and advantages of the present invention will be apparent to one skilled in the art from the following detailed description, connection with the accompanying drawings.

DETAILED DESCRIPTION

Figure 1:
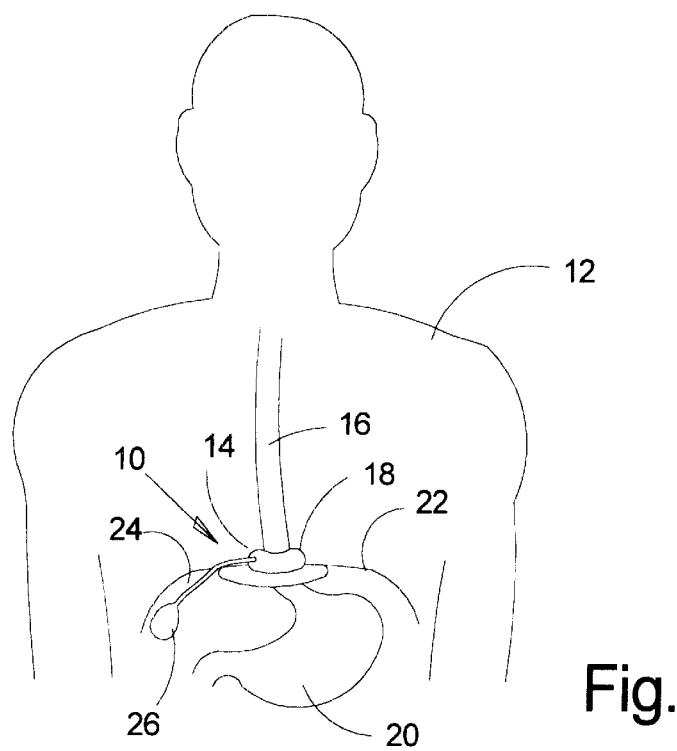
FIG. 1 is a representation of a patient with a prosthetic sphincter apparatus according to my invention implanted near the lower esophageal sphincter of the patient.

I will now describe my invention with reference to the accompanying drawings, wherein like numerals are used to describe like parts in the various views. FIG. 1 illustrates an implantable esophageal sphincter apparatus 10 in a patient 12. The apparatus 10 comprises a toroidal sphincter body 14 that is placed around the esophagus 16 of the patient 12 adjacent the lower esophageal sphincter 18. The sphincter body 14 would usually be implanted above the patient's stomach 20 and preferably immediately above the diaphragm 22. The diaphragm is a domed, muscular layer of tissue separating the abdomen and the thorax. A tube 24 connects the sphincter body 14 to a control apparatus 26 that regulates the size of the sphincter body 14, as explained hereafter.

Figure 2:
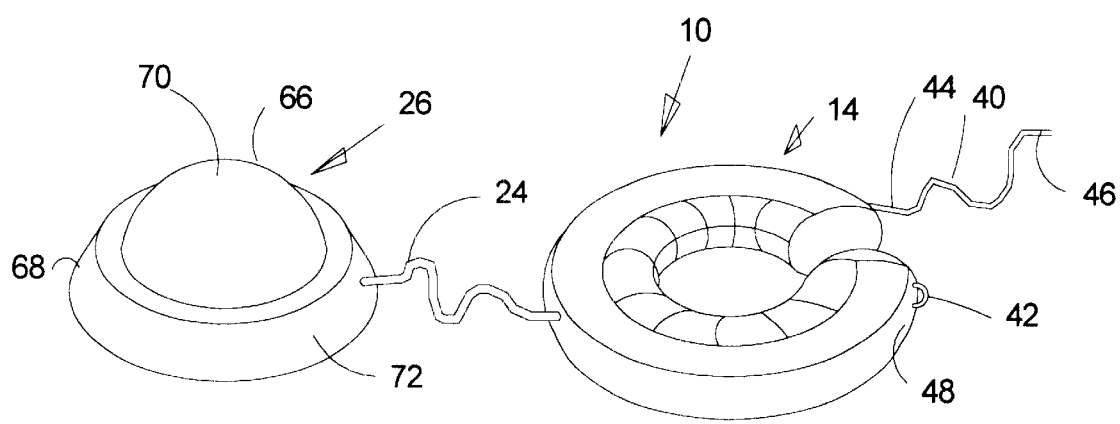
FIG. 2 is a perspective view of an implantable prosthetic sphincter apparatus according to the present invention.
Figure 3:
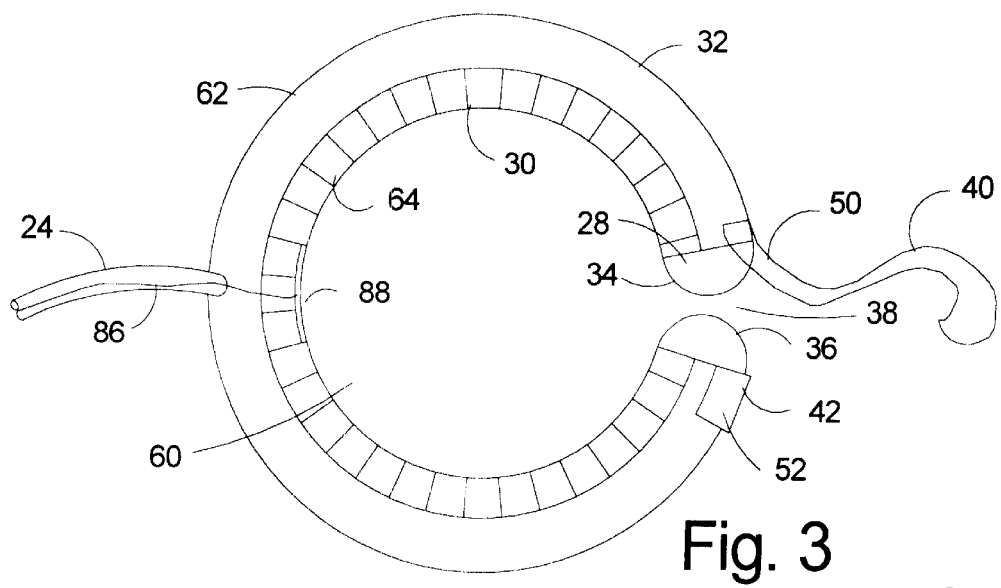
FIG. 3 is a top plan view of the prosthetic sphincter apparatus of FIG. 2.
Figure 7:
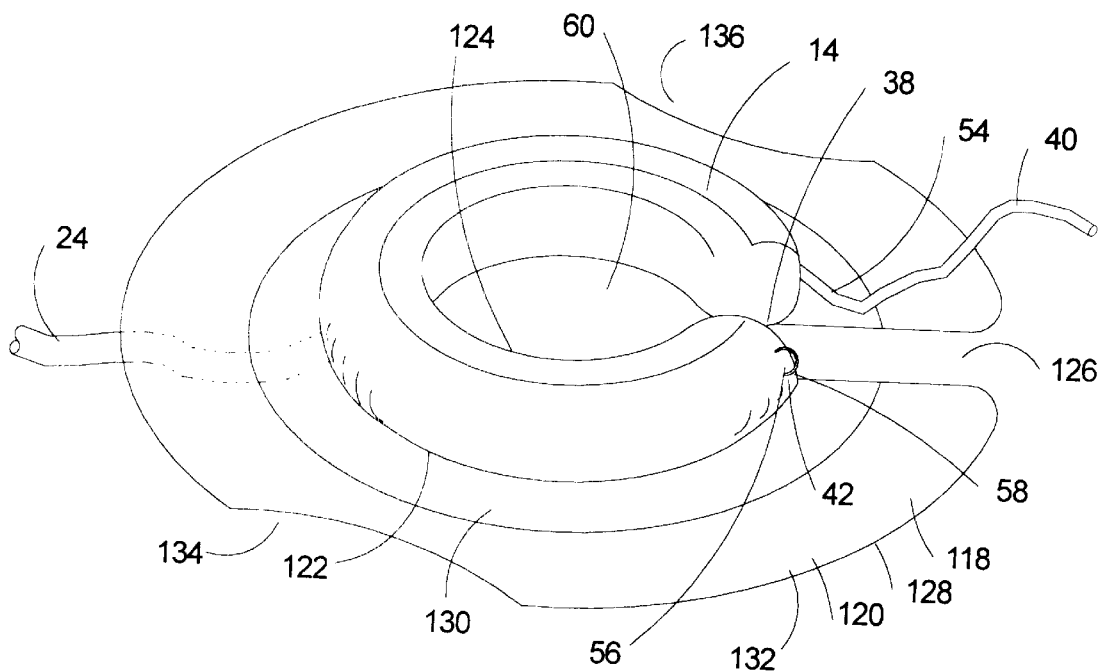
FIG. 7 is a perspective view of an implantable esophageal sphincter body with diaphragm shield.

The sphincter body 14 comprises a generally toroidal inflatable bladder 28 having an inner wall 30 and an outer wall 32. Preferably, the bladder 28 also has a first end 34 and a second end 36 forming a gap 38. Viewed from above, as in FIG. 3, the sphincter body forms a "C", a structure that allows the sphincter body 14 to be placed around the esophagus 16 by passing the esophagus through the gap 38. A clasp 40 on the outer wall 32 near the first end 34 connects to an anchor 42 on the outer wall 32 near the second end 36, allowing the two ends to be tied together after the sphincter body 14 has been placed around the patient's esophagus. The clasp and anchor may take any suitable form. For example, the clasp 40 may be a pre-threaded suture 44 with attached needle 46 having a distal end permanently attached to the sphincter body, as illustrated in FIG. 2, and the anchor 42 may be a sewing tab 48. Alternatively, sewing tabs could be provided on both the first and second ends and an ordinary prethreaded suture could be threaded through both tabs to hold the ends together. Another type of clasp 40 is shown in FIG. 3. The clasp 40 may comprise a strip 50 of hook-and-eye fastener, and the anchor 42 may be a mating piece 52 of hook-and-eye material. A third embodiment of a clasp 40, as shown in FIG. 7, may comprise an elastomeric filament 54 having teeth along one side. The filament 54 engages a receptacle 56 having an opening 58 with a spring latch for connecting with the teeth, in the manner of a cable tie. After the gap is closed, excess length of the male filament could be trimmed away. Other specific forms for the clasp and anchor will suggest themselves to one of skill in the art.

When the sphincter body 14 has been placed around the esophagus, it is desirable to control the size of a central opening 60 through the sphincter body 14. The inflatable bladder tends to expand radially when filled with fluid. An inextensible outer surface 62 adjacent the outer wall 32 of the bladder 28 constrains the bladder so that the central opening 60 becomes smaller rather than larger as the bladder is filled. The surface 62 may be an inextensible polymeric substance such as polyamide. It may also be a rigid structure of, for example, titanium, Elgiloy (trademark) steel, or other implantable material.

The lower esophageal sphincter allows food to pass from the esophagus into the stomach, but prevents acidic stomach contents from entering and damaging the esophagus. This can be accomplished without completely closing the sphincter. Thus, if the sphincter body 14 can restore some of the effectiveness of the sphincter by partially closing the sphincter. Food can still pass into the stomach, but either acid or bilious reflux is minimized or eliminated, without continually adjusting the sphincter body. It is important, therefore, that the sphincter body close only to a predetermined minimum diameter. A relatively inextensible, flexible skin 64 adjacent the inner wall of the bladder 28 and connected to the inextensible outer surface, prevents the sphincter body from closing completely, and preferably from completely closing the lower esophageal sphincter within the sphincter body 28. Preferably, the minimum inside diameter of the esophagus should be not less than about 45 French (15 mm), and more preferably not less than about 54 French (18 mm). Such an opening will allow food to be swallowed, yet inhibit either acid or bilious reflux. The wall of the esophagus is usually between 2 mm or 3 mm thick. The central opening 60 of the sphincter body should be not less than about 57 French (19 mm), or more preferably not less than about 66 French (22 mm). In some patients, the benefits may be obtained with a larger central opening, allowing larger portions of food to be swallowed comfortably. Less inflation of the bladder produces a larger central opening.

The control apparatus 26 regulates the amount of a fluid, such as normal saline solution, that fills the sphincter body 14. Although the control apparatus 26 may adjoin the sphincter body 14, it is preferable that the control apparatus be spaced away from the sphincter body in a more accessible area of the body. A tube 24 with at least one lumen for carrying fluid to and from the sphincter body 14 connects the sphincter body and the control apparatus. A control apparatus illustrated in FIG. 2 comprises an implantable chamber 66 having a fluid container 68 with a pierceable septum 70. The tube 24 communicates with the fluid container 68 through a nipple 72. The chamber 66 is implanted beneath the patient's skin and is accessible by a needle inserted through the skin and septum 70. Fluid can be inserted into or withdrawn from the chamber 66 with a syringe. The fluid will, in turn, inflate or deflate the bladder in the sphincter body, thereby enlarging or decreasing the size of the central opening 60.

Figure 4:
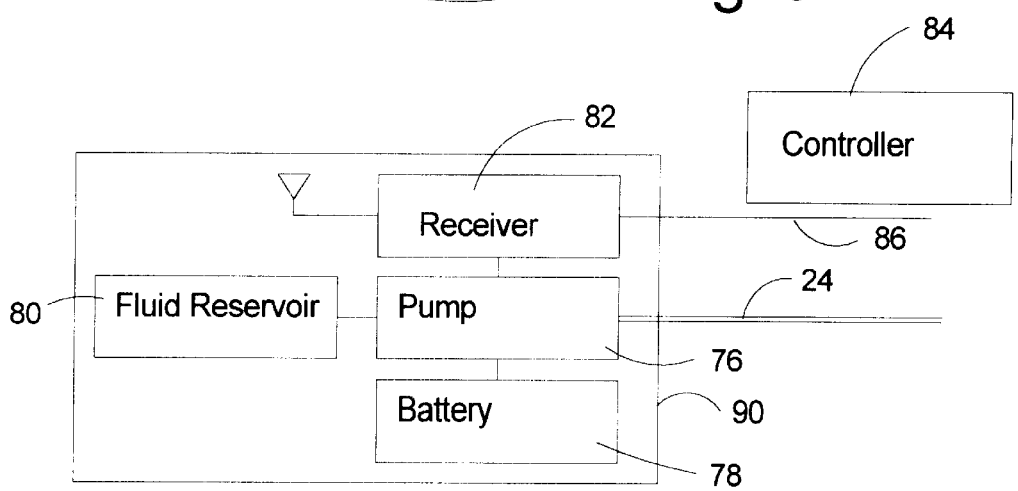
FIG. 4 is a block diagram of a control mechanism for use with the apparatus of the present invention.

The control apparatus 26 may also be an implantable electrically controlled pump 74, illustrated in block diagram in FIG. 4. The electrically controlled pump 74 comprises a bi-directional fluid pump 76 connected to a battery power supply 78, a fluid reservoir 80, and the tube 24 leading to the sphincter body. A receiver-controller 82 receives instructions transmitted from an external control device 84 and causes the pump 76 to move fluid into or out of the sphincter body. An electrical conductor 86 connects the controller 82 to a sensor 88, such as a strain gauge or a pressure sensor, mounted on the sphincter body 14 (FIG. 3). In response to detected changes, the electrically controlled pump 74 may decrease or increase the central opening 60. The sensors 88 could also detect whether the increased pressure is on the upper (or esophageal) side of the sphincter body or on the lower (or stomach) side, and respond accordingly. For example, increased pressure on the upper side may indicate that the patient is attempting to swallow, and the central opening may need to be enlarged. Increased pressure on the lower side may indicate an increased chance for either acid or bilious reflux, and the central opening may need to be reduced. The receiver 82, fluid reservoir 80, pump 76 and battery 78 should all be enclosed in a case 90 which is impervious to body fluids. Suitable titanium cases are well known from other types of implantable medical devices, for example, implantable pacemakers.

Figure 5:
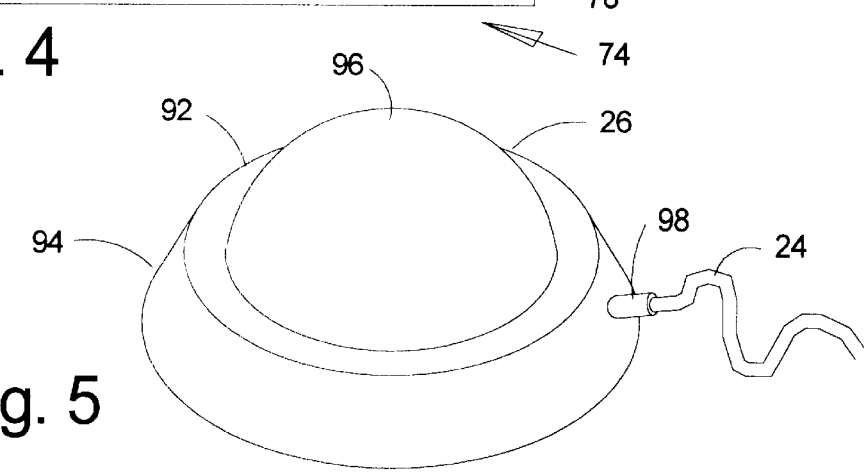
FIG. 5 is a perspective view of a manual pump for use with the present invention.
Figure 6:
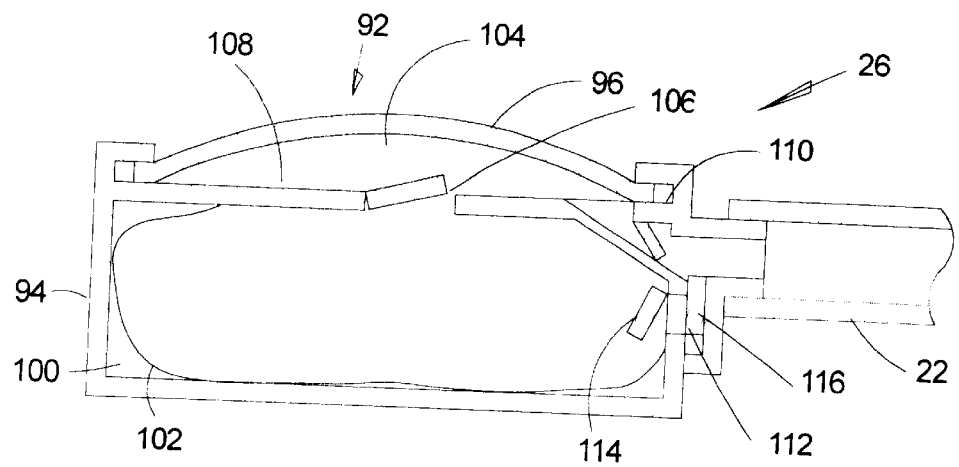
FIG. 6 is a through section view of the manual pump of FIG. 5.

A third example of a control apparatus 26 is shown in FIGS. 5 and 6. The apparatus is a manually controlled pump 92. The manually controlled pump 92 has a case 94 with a deflectable diaphragm 96 and a reversible valve 98. The reversible valve 98 communicates with the tube 24. As seen best in FIG. 6, the manually controlled pump 92 has a chamber 100 inside the case 94. A collapsible bag 102 in the chamber contains a supply of fluid. The bag communicates with a pumping chamber 104 under the deflectable diaphragm 96 through a one-way valve 106 in a partition 108. The partition 108 separates the chamber 100 and collapsible bag 102 from the pumping chamber 104. The manually controlled pump 92 is implanted beneath the skin of the patient so that the patient can press on the diaphragm 96 and force fluid through a second one-way valve 110 into the tube connected to the sphincter body. This action will fill and expand the sphincter body, decreasing the size of the central opening, and closing the esophagus. To reverse the flow and open the sphincter body, the patient would place a magnet over the manually controlled pump 92. The magnet displaces a metallic dam 112 from a normal position covering a third one-way valve 114 to a temporary position blocking the second one-way valve 110. A small leaf spring 116 holds the metallic dam 112 in its normal position, but it is not strong enough to resist the magnetic attraction applied to the metallic dam 112. With the third valve 114 exposed, fluid flows back into the bag 102, driven by the elastic bladder in the sphincter body. The patient is thereby able to adjust the opening in the sphincter body within the limits imposed by the inextensible outer surface 62 and the inextensible, flexible skin 64.

The esophagus passes through a "hiatus", or opening, in the diaphragm before reaching the stomach. As a consequence either of the physical debilities attending acid reflux disease or of the surgery recommended to treat the disease, the esophageal hiatus may become enlarged and a hiatus hernia may develop. A hiatus hernia is a protrusion of the stomach upward into the mediastinal cavity through the esophageal hiatus of the diaphragm. To correct or to avoid the development of this condition, a shield 118 may be provided on the sphincter body 14. The shield 118 comprises a generally circular sheet 120 of biologically compatible material attached to a distal side 122 of the sphincter body 14. Suitable materials may be knitted or woven Dacron (trademark) cloth or Gore-Tex (trademark) material. The sheet 120 has an opening 124 corresponding to the central opening 60 of the sphincter body 14. A slot 126 extends through the sheet 120 from the gap 38 in the sphincter body 14 to an outer edge 128 of the sheet 120. Additional slots may be provided to allow the sheet to conform to the concave underside of the diaphragm, or the sheet may be shaped to approximate the expected shape of the diaphragm.

An interior region 130 of the sheet adjacent the sphincter body 14 and extending a selected distance radially outward from the sphincter body 14 is relatively stiff and provides a barrier at the esophageal hiatus. An outer region 132 between the inner region 130 and the outer edge 128 is more flexible and may be adapted to encourage tissue growth into the material of the outer region. This would tend to anchor the shield 118 to the diaphragm. The shield may also the sutured to the diaphragm, particularly posteriorly near the crura of the diaphragm, that is, to the tissues connecting the diaphragm to the back. A notch 134 may be provided in the right anterior part of the outer region 130 so that the shield would not be in contact with the lower vena cava. Similarly a second notch 136 at the anterior side of the shield so that the shield would not be in contact with the descending aorta. The tube 24 should be connected to the distal side 122 of the sphincter body 14 and extend through the shield 118. To implant the apparatus, the sphincter body 14 would preferably be pushed through the diaphragm like a plug, thereby bringing the shield 118 to rest adjacent the distal, or bottom, side of the diaphragm. The tube 14 and control apparatus 26 would be implanted in the abdominal cavity.

Although I have now described my invention in connection with my preferred embodiment, those skilled in the art will recognize that my invention may take other forms without departing from the spirit or teachings thereof. The foregoing description is intended, therefore, to be illustrative and not restrictive, and the scope of my invention is to be defined by the following claims .

What is claimed is:

1. An implantable apparatus for supporting the lower esophageal sphincter of a patient the apparatus comprising
   a toroidal inflatable bladder having
   an outer circumferential wall and
   an inner circumferential wall, said inner circumferential wall defining an orifice through which the esophagus of a patient may pass, said inner circumferential wall being movable inwardly such that the size of said orifice can be reduced to a predetermined minimum area, said minimum area being large enough such that a lower esophageal sphincter received within said orifice could not be fully closed by action of said apparatus, and
   a shield connected to said toroidal bladder, said shield comprising a sheet extending radially outwardly from said toroidal bladder, said sheet comprising an inner circumferential area adjacent said sphincter body and an outer circumferential area spaced radially outwardly from said sphincter body beyond said inner circumferential area, said inner area being stiffer than said outer area.

2. The implantable apparatus of claim 1 wherein said minimum area has a diameter not less than about 57 French (19 mm).

3. The implantable apparatus of claim 2 wherein said diameter is not less than about 66 French (22 mm).

4. The implantable apparatus of claim 1 said minimum area is large enough to permit food to be swallowed through the lower esophageal sphincter.

5. The implantable apparatus of claim 1 further comprising a rigid constraining wall adjacent said outer circumferential wall.

6. The implantable apparatus of claim 5 wherein said constraining wall further comprises a relatively inextensible, flexible skin.

7. The implantable apparatus of claim 6 wherein said skin surrounds said inflatable bladder.

8. The implantable apparatus of claim 1 further comprising an inflatable bladder and a relatively inextensible skin surrounding said inflatable bladder.

9. The implantable apparatus of claim 1 wherein said toroidal bladder has a first end and a second end, said ends lying near each other and defining a longitudinal opening from said outer wall to said inner wall.

10. The implantable apparatus of claim 9 further comprising a clasp releasably connecting said first and second ends.

11. The implantable apparatus of claim 9 further comprising a rigid constraining wall adjacent said outer circumferential wall.

12. The implantable apparatus of claim 11 wherein said constraining wall further comprises a relatively inettensible, flexible skin.

13. The implantable apparatus of claim 12 wherein said skin surrounds said inflatable bladder.

14. The implantable apparatus of claim 11 further comprising a clasp releasably connecting said first and second ends.

15. The implantable apparatus of claim 1 further comprising a pump in fluid communication with said bladder for adjusting the size of said bladder.

16. The implantable apparatus of claim 15 wherein said pump is implantable.

17. The implantable apparatus of claim 16 wherein said pump is manually controlled.

18. The implantable apparatus of claim 16 further comprising a sensor mounted on said bladder and electrically connected to a controller, said controller causing said pump to inflate or deflate said bladder in response to signals from said sensor.

19. The impliritable apparatus of claim 1 wherein said sheet is connected to a side of said toroidal bladder.

20. The implantable apparatus of claim 19 wherein said bottom side is adapted to lie near the stomach and wherein said sheet is connected to said
    bottom side of said toroidal bladder.

21. The implantable apparatus of claim 1 wherein said sphincter body has two ends defining a gap and wherein said sheet has a slot extending radially outwardly from said gap.

22. A method for treating gastroesophageal reflux disease comprising the steps of
    placing a toroidal inflatable bladder around the lower esophageal sphincter of the patient, said inflatable bladder having an outer circumferential wall and an inner circumferential wall, said inner circumferential wall defining an orifice through which the esophagus of the patient is passed, said orifice having a predetermined minimum size,
    connecting a shield to said bladder, said shield comprising a sheet extending radially outwardly from said bladder, said sheet comprising an inner circumferential area adjacent said bladder and an outer circumferential area spaced radially outwardly from said bladder and beyond said inner circumferential area, said inner area being stiffer than said outer area,
    positioning said sheet adjacent a bottom side of a patients diaphragm, and inflating said bladder to partially close the lower esophageal sphincter.

23. The method of claim 22 wherein the esophageal sphincter is closed to a diameter of not less than 57 French (19 mm).

24. The method of claim 23 wherein said diameter is not less than about 66 French (22 mm).

25. The method of claim 22 wherein the bladder is selectively inflated and deflated.

26. The method of claim 25 wherein the inflation and deflation of the bladder can be manually controlled.

27. The method of claim 25 wherein the inflation and deflation of the bladder is controlled by a sensor.

28. The method of claim 22 wherein said bladder further comprises an upper side connecting said inner wall and said outer wall and a bottom side connecting said inner wall and said outer wall and wherein said sheet is connected to a side of said bladder.

29. The method of claim 22 wherein said bladder has two ends defining a gap and wherein said sheet has a slot extending radially outwardly from said gap and further comprising passing the esophagus of a patient through said slot and said gap.

30. An implantable apparatus for supporting the lower esophageal sphincter of a patient, the apparatus comprising
    a toroidal sphincter body having an outer circumferential wall and an inner circumferential wall, said inner circumferential wall defining an orifice through which the esophagus of a patient may pass, and a shield connected to said sphincter body, said shield comprising a sheet extending radially outwardly from said sphincter body, said sheet comprising an inner circumferential area adjacent said sphincter body and an outer circumferential area spaced radially outwardly from said sphincter body and from said inner circumferential area, said inner area being stiffer than said outer area.

31. The implantable apparatus of claim 30 wherein said sphincter body further comprises an upper side connecting said outer wall and said inner wall and a bottom side connecting said outer wall and said inner wall and wherein said sheet is connected to a side of said sphincter body.

32. The implantable apparatus of claim 31 wherein said bottom side is adapted to lie near the stomach and wherein the sheet is connected to said bottom side.

33. The implantable apparatus of claim 30 wherein said sphincter body has two ends defining a gap and wherein said sheet has a slot extending radially outwardly from said gap.

34. An implantable apparatus for supporting the lower esophageal sphincter of a patient, the apparatus comprising a toroidal sphincter body having
an outer circumferential wall and
an inner circumferential wall, said inner circumferential wall defining an orifice through which the esophagus of a patient may pass, and a flexible sheet connected to said sphincter body, said sheet extending radially outwardly from said sphincter body.

35. The implantable apparatus of claim 34 wherein said flexible sheet is adapted to rest adjacent a bottom side of the diaphragm of a patient when said toroidal sphincter body is passed through said diaphragm.

* * * * *